United States Patent [19]

Jochim et al.

[11] Patent Number: 4,678,746

[45] Date of Patent: Jul. 7, 1987

[54] MONOCLONAL ANTIBODIES TO EPIZOOTIC HEMORRHAGIC DISEASE VIRUS ANTIGEN

[75] Inventors: Michael M. Jochim, Arvada; Suzanne C. Jones, Lakewood, both of Colo.

[73] Assignee: The United States of America as represented by the Secretary of Agriculture, Washington, D.C.

[21] Appl. No.: 708,613

[22] Filed: Mar. 5, 1985

[51] Int. Cl.$^4$ .................... G01N 33/577; C12Q 1/70
[52] U.S. Cl. ........................................ 435/5; 435/7; 435/68; 435/172.2; 435/240; 435/241; 435/948; 436/548; 436/800; 530/387; 530/388; 935/89; 935/93; 935/95; 935/96; 935/99; 935/100; 935/104; 935/106; 935/110
[58] Field of Search ................... 435/517, 68, 172.2, 435/240, 241, 948; 436/548; 530/387, 388; 935/89, 93, 95, 96, 99, 100, 104, 106, 110

[56] References Cited

PUBLICATIONS

M. M. Jochim and S. C. Jones, "Identification of BT and EHD Viruses by Immunofluorescence with Monoclonal Antibodies," Proceedings of the American *Association of Veterinary Laboratory Diagnosticians*, pp. 277-286 (1983) (oral presentation, 1983; printed publication mailed to members about Apr. 15, 1984).

American Association of Veterinary Laboratory Diagnosticians, Inc. *Newsletter*, p. 28 (Mar. 1983).

G. Kohler and C. Milstein, "Continuous Cultures of Fused Cells Secreting Antibody of Predefined Specificity," *Nature*, vol. 256, pp. 495-497 (1975).

G. Kohler and C. Milstein, "Derivation of Specific Antibody-Producing Tissue Culture and Tumor Lines by Cell Fusion," *European Journal of Immunology*, vol. 6, pp. 511-519 (1976).

G. Galfre, S. C. Howe and C. Milstein, "Antibodies to Major Histocompatibility Antigens Produced by Hybrid Cell Lines," *Nature*, vol. 266, pp. 550-552 (1977).

*Monoclonal Antibodies, Hybridomas: A New Dimension in Biological Analyses*, R. H. Kennett, T. J. McKearn, and K. B. Bechtol, Eds., Plenum Press, New York and London (1980).

M. Shulman, C. D. Wilde, and G. Kohler, "A Better Cell Line for Making Hybridomas Secreting Specific Antibodies," *Nature*, vol. 276, pp. 269-270 (1978).

M. M. Jochim, T. L. Barber, and B. M. Bando, "Identification of Bluetongue and Epizootic Hemorrhagic Disease Viruses by the Indirect Fluorescent Antibody Procedure," *Proceedings of the American Association of Veterinary Laboratory Diagnosticians*, pp. 91-103 (1974).

D. W. Verwoerd, H. J. Els, E. M. Devillers, and H. Huisman, "Structure of Bluetongue Virus Capside," *Journal of Virology*, vol. 10, pp. 783-794 (1972).

M. M. Jochim and S. C. Jones, "Plaque Neutralization of Bluetongue Virus and Epizootic Hemorrhagic Disease Virus in BHK$_{21}$ Cells," *American Journal of Veterinary Research*, vol. 37, pp. 1345-1347 (1976).

*Selected Methods in Cellular Immunology*, B. B. Mishell and S. M. Shiigi, Eds., W. H. Freeman and Co., San Francisco, pp. 6-8 (1980).

R. H. Kennett, K. A. Denis, A. S. Tung, N. R. Klinman, "Hybrid Plasmacytoma Production: Fusions with Adult Spleen Cells, Monoclonal Spleen Fragments, Neonatal Spleen Cells and Human Spleen Cells," *Current Topics in Microbiological Immunology*, vol. 81, pp. 77-91 (1978).

*Primary Examiner*—Christine M. Nucker
*Attorney, Agent, or Firm*—M. Howard Silverstein; David G. McConnell; Margaret A. Connor

[57] ABSTRACT

A method for preparing hybrid cell lins (hybridomas) which secrete monoclonal antibody which is group-specific to epizootic hemorrhagic disease virus antigen and which does not react to antigenically-related bluetongue virus antigen is disclosed. The antibody identifies EHDV in infected cell cultures with immunofluorescence and provides a means for ready diagnosis of EHDV in animals.

11 Claims, No Drawings

MONOCLONAL ANTIBODIES TO EPIZOOTIC HEMORRHAGIC DISEASE VIRUS ANTIGEN

BACKGROUND OF THE INVENTION

The invention relates to a process for producing monoclonal antibodies to epizootic hemorrhagic disease virus antigen and to the hybrid cell lines that secrete these monospecific antibodies.

Epizootic hemorrhagic disease (EHD) is an infectious, non-contagious, insect-transmitted virus disease that affects primarily wild ruminants and cattle. Epizootic hemorrhagic disease virus (EHDV) is classified as an Orbivirus and is antigenically related to bluetongue virus (BTV), also an Orbivirus. Two distinct serotypes of EHDV are known to exist in the United States, and seven or more exist worldwide. The two U.S. serotypes were initially isolated from clinically sick deer but are commonly isolated from cattle, wild ruminants, and the suspected vector, *Culicoides variipennis*.

EHDV infection of white-tailed deer and antelope is most often a peracute infection with a high rate of morbidity and mortality. The disease in cattle is usually subclinical with only mild signs similar to infection with BTV. However, economic losses due to EHDV infections in cattle result from restrictions to export markets and to a lesser extent, from clinical infection. Because EHDV and BTV clinical infections in cattle are so similar, a definitive diagnosis cannot be made without conducting proper laboratory tests.

Additionally, because these two viruses are antigenically related, that is, the antibodies produced by the animal in response to infection with one virus may cross-react in the laboratory when tested against the other one, to accurately diagnose EHDV or BTV it is necessary to isolate the viral agent and correctly identify the isolated virus.

One laboratory test that has been used to differentiate between EHDV and other viruses is the indirect fluorescent antibody test (IFAT), which uses hyperimmune rabbit serum taken from EHDV-inoculated rabbits to visualize viral antigen in virus-infected cell cultures. Because EHDV and BTV "share" antigenic sites on some of the viral proteins, even the most specific rabbit antibody to EHDV will contain antibodies that cross-react with BTV antigens. Recently, M. M. Jochim and S. C. Jones developed monospecific (monoclonal) antibodies which identify BTV in infected cell cultures and which do not react with EHDV antigen in infected cells. These are described in U.S. patent application Ser. No. 570,155. What is needed is a monoclonal antibody that will identify either of the two serotypes of EHDV in the same way that monoclonal antibodies have been produced and used to identify BTV. In this way the diagnosis of BTV-EHDV would be simple and complete with essentially no possibility of misidentification of these two closely related animal viruses.

The production of monoclonal antibodies by the fusion of spleen cells from immunized mice and myeloma cells grown in continuous culture, has been described previously, e.g., Kohler et al. in Nature, Vol. 256, pp. 495–497 (1975), Kohler et al. in *European Journal of Immunology*, Vol. 6, pp. 511–519 (1976), Galfre et al. in Nature, Vol. 266, pp. 550–552 (1977), and in the text *Monoclonal Antibodies, Hybridomas: A New Dimension in Biological Analysis*, R. Kennett, T. McKearn, K. Bechtol, Eds., Plenum Press, New York and London (1980). Techniques for the chemical selection of hybridomas arising from such a fusion, and subsequent isolation of single antibody secreting cell clones for the production of the monoclonal antibodies are also known. However, no cell lines have been produced capable of secreting monoclonal antibodies which are group-specific to EHDV and not serotype-specific, that is, which recognize either EHDV serotype 1 or serotype 2, which do not give false positive reactions to closely related viruses such as BTV, and which have been shown to be useful for identification of EHD viral antigens using common, simple tests such as immunofluorescence.

It should be noted that because of the unpredictable nature of hybrid cell preparation, one cannot extrapolate from one antigen or cell system to another.

SUMMARY OF THE INVENTION

We have prepared hybrid cell lines which secrete monoclonal antibodies to EHDV which are group-specific rather than serotype-specific and which do not cross-react with any of the five different serotypes of BTV known to be present in the United States. Because these novel antibodies produced by the hybridomas of our invention are groupspecific in their recognition of either of the two serotypes of EHDV found in the United States but do not react with any of the five serotypes of BTV, it will be possible to apply these antibodies with almost absolute assurance that EHDV can be accurately identified in the laboratory, thereby enhancing the speed and accuracy of diagnosis.

Also, because the monoclonal antibodies of the invention identify EHDV in infected cell cultures with immunofluorescence, they provide a means for ready diagnosis of EHD using simple tests such as the IFAT which is comaon to most diagnostic laboratories.

In accordance with this discovery, it is an object of the invention to provide hybridomas which produce antibodies which are group-specific to EHDV and do not react with BTV.

It is also an object of the invention to provide methods for preparing these hybridomas.

It is a further object of the present invention to provide antibodies which react with a group-specific EHD viral antigen and do not recognize the antigenic determinants associated with BTV and to provide methods of preparing these antibodies.

A still further object of the invention is to provide methods for ready identification and diagnosis of EHDV and differentiation of this virus from other closely related orbiviruses using these antibodies, and to provide a method of visualizing EHD viral-specific antigens in cell cultures.

Other objects and advantages of this invention will become readily apparent from the ensuing description.

DETAILED DESCRIPTION OF THE INVENTION

The method of preparing the hybridomas comprises the following steps:

Mice are injected with epizootic hemorrhagic disease virus (EHDV) to stimulate (immunize) the lymphocyte population to produce antibodies (immunoglobulins) to the viral antigens associated with the virus and the viral antigens associated with the replication of the virus in the animal. After a period of time and a series of injections the mice are stimulated one last time by intravenous inoculation of virus, and 3 days later the spleens are removed for subsequent cell fusion experiments.

Next, myeloma cells that have the capability of continuous growth in cell culture medium and spleen cells that are secreting specific antibodies after stimulation, as described above, are fused to form hybrid cells (hybridomas) that have characteristics of the parental cells. Hybridomas are selected from the parental myeloma cells on the basis of the sensitivity of the myeloma cells to medium that contains hypoxanthine-aminopterin-thymidine (HAT). Myeloma cells useful for this invention lack the enzyme hypoxanthine phosphoribosyl transferase, and thus die in HAT selective medium. Exemplary myeloma cells for this invention are SP2/0-Ag14, which are derived from a hybrid that was produced from BALB/c spleen cells and X63-Ag8, a cell line frequently used to produce hybridomas as described by Shulman et al. in *Nature*, Vol. 276, pp. 269–270 (1978). In addition to their sensitivity to HAT medium these cells are resistant to 20 μg/ml of 8-azaguanine and synthesize no immunoglobulin. The advantage of fusing a non-immunoglobulin secreting myeloma cell is that any immunoglobulin associated with the growth of hybridomas arising from the fusion will indicate a contribution from the spleen cell.

The myeloma cells are maintained in suitable growth medium such as Dulbecco's Modified Eagle Medium that contains fetal bovine serum, 2-mercaptoethanol, and 8-azaguanine; incubation of cultures in this medium is at 37° C. under 7% $CO_2$ tension and 95% humidity. Cells are subcultured every day for 3 days prior to fusion.

Suitable techniques for cell fusion to obtain hybridomas are described in Kennett et al. in *Current Topics in Microbiological Immunology*, Vol. 81, pp. 77–91 (1978) and in *Monoclonal Antibodies, Hybridomas: A New Dimension in Biological Analysis*, R. Kennett, T. McKearn, K. Bechtol, Eds., Plenum Press, New York & London (1980). Basically, the spleen cells and the myeloma cells are fused in the presence of polyethylene glycol (PEG). Feeder cells such as mouse peritoneal macrophages can be added to the fusion mixture to aid in the establishment of hybridomas. The cell suspension is diluted in the appropriate medium and 50 μl added to each well of a 96-well cell culture plate. After 1 day of incubation at 37° C., under 5% $CO_2$ and 95% humidity, each well receives a drop of medium containing HAT to kill the myeloma cells while permitting growth of the hybrids. Small colonies of hybridomas can be seen within about 5 days after the fusion and when they are about 2 mm in diameter they can be transferred to new microplates using a pasteur pipette to transfer a single colony to an individual well. Hybridomas are propagated in medium containing HAT and the spent medium tested for the presence of immunoglobulin and for the presence of antibodies specific for the viral antigen of interest. A number of different serologic tests are known for evaluating the antibodies secreted by the various hybridomas. In the process of this invention, a preferred method of selecting hybridomas which secrete the novel antibodies which react to group-specific EHDV antigen determinants but not to BTV antigen is on the basis of the reaction of antibodycontaining hybridoma fluids in the indirect fluorescent antibody test (IFAT) using EHDV-infected cell cultures and fluorescein isothiocyanate conjugated anti-mouse IgG to visualize the antigen-antibody reaction. Antibodies are selected which react with group-specific EHDV antigen in the IFAT, do not react with BTV antigen in the IFAT, and do not react with uninfected Vero cultured cells in the IFAT. This use of EHDV group-specific nonoclonal antibody in the IFAT has not been disclosed previously. The IFAT is particularly useful because the antibody is monospecific for EHDV only and cell cultures infected with BTV will be obviously negative.

After unique hybridomas are identified they are cloned such as by limiting dilution techniques to establish, from a single hybridoma cell, antibody-producing cell clones which can then be propagated indefinitely.

The group-specificity of antibodies to EHDV is determined by testing against each of the two serotypes of EHDV present in the United States, namely, EHDV serotypes 1 (New Jersey) and 2 (Alberta). Antibodies which react to both serotypes 1 and 2 are concluded to be reacting with common polypeptides and are designated to be group-specific. Next, the antibodies are tested for reactivity to BTV serotypes 2, 10, 11, 13, and 17 which have been shown to cross-react with EHDV in other tests. Antibodies which do not react with the five BTV serotypes are designated as not recognizing the antigenic determinants associated with BTV.

One of the hybridomas obtained by the present invention is a monoclone which secretes IgG antibody which reacts with viral antigen present in cell cultures infected with both serotypes of EHDV present in the United States and does not react with cell cultures infected with any of the five serotypes of BTV (2, 10, 11, 13, and 17) which have been shown to cross-react in other serological tests for EHDV. The monoclone is identified as EHDV2XSP2/0-Ag14-11C6.288. The monoclone has been deposited with the American Type Culture Collection, Rockville, Md., and has been assigned the designation HB 8378.

Because of the specificity of the monoclonal antibodies produced by the cloned hybridomas for antigenic sites associated with EHDV, they can be used to identify the presence of EHDV antigen in infected cultured cells to diagnose epizootic hemorrhagic disease. Because the antibodies of the invention identify EHDV with immunofluorescence, they can be used in the IFAT to provide a simple and accurate diagnostic test for EHDV in animals. In such a diagnostic procedure, virus from the infected animal is isolated and adapted to grow in a cell culture. EHDV is identified by applying the IFAT using monoclonal antibody of the invention which reacts with group-specific EHDV antigen in the IFAT, does not react with BTV antigen in the IFAT, and does not react with uninfected Vero cultured cells used in the IFAT, in combination with fluorescein isothiocyanate conjugated rabbit anti-mouse IgG.

The antibodies of the invention can also be used to identify EHDV antigens associated with infected tissues such as blood cells and histologic sections of organs taken from diseased animals. In either case the monoclonal antibodies can be used in combination with or coupled to an immunochemical such as fluorescein isothiocyanate, peroxidase, alkaline phosphatase or other such reagent. The antibody can also be used for development of "antigen capture" techniques whereby the antibody is first attached to a plastic substrate and then blood or tissue suspensions from infected animals are brought in contact with the antibody, which "captures the viral-antigen," and preserves it for subsequent identification. Because of the specificity of the antibody it can be used to differentiate EHD virus from other closely related orbiviruses such as BTV.

EXAMPLE

The following example illustrates the present invention and is not intended to limit the same.

A. Preparation of EHDV for Mouse Inoculation

The virus used to immunize mice was strain Alberta of EHDV serotype 2 that had been partially purified by a modification described below of the procedure of Verwoerd et al. in *Journal of Virology,* Vol. 10(4), pp. 783–794 (1972). Monolayer cultures of BHK-21 cells in $690^2$ cm glass roller bottles were infected with the eighth cell culture passage of EHDV and cells were harvested and separated from the culture fluid when 75% or more of the cells appeared infected. After centrifugation at 1500×g the cells were suspended in 0.002M Tris-HCl buffer (pH 8.8), using a volume equal to 1/160th of the volume of the original cell culture fluid. The cells were further disrupted by insonation (Model S 125, Branson Sonic Power Company, Plainview, N.Y.) for 2 minutes in an ice-water bath. A 1% suspension of Sephadex G-200 (Pharmacia Laboratories Inc., Piscataway, N.J.) in Tris buffer, was added at a tenth volume of the Tris buffer. Genesolv-D (trichlorotrifluoroethane, Allied Chemical Corp., Morristown, N.J.) was then added at a third of the total volume. The mixture was shaken vigorously for 3 to 5 minutes and centrifuged at 2000×g for 30 minutes. The supernate was removed and saved and the cells extracted a second time with fresh Tris buffer and Genesolv-D. The supernate from both extractions was pooled, diluted 1:1 (v/v) with buffered lactose peptone, and stored at −70° C. The infectivity of the virus was determined by titration in BHK-21 cells as described by Jochim et al. in *American Journal of Veterinary Research,* Vol. 37, pp. 1345–1347 (1976).

B. Immunization of Mice

Adult, female, BALB/c mice were immunized by two intraperitoneal injections of $5.3\times10^6$ and $2.6\times10^6$ plaque forming units (PFU) of EHDV, given approximately 6 weeks apart. After 3 weeks the mice were injected with $2.6\times10^6$ PFU of EHDV intravenously.

C. Preparation of Spleen Cells for Fusion

The spleen cell suspension was prepared in the manner described by R. H. Kennett, "Fusion Protocols," in: *Monoclonal Antibodies, Hybridomas: A New Dimension in Biological Analysis,* R. Kennett, T. McKearn, K. Bechtol, Eds., Plenum Press, New York & London, pp. 365–367 (1980). Spleens were removed aseptically from immunized mice 3 days after the last injection of EHDV and held in HY medium as formulated by Kennett. This medium consisted of Dulbecco's Modified Eagle Medium (with 4.5 g/l liter of glucose and 4mM glutamine) plus 10% NCTC 109 (Microbiological Associates, Los Angeles, Calif.), fetal bovine serum (20%) that had been screened for high cloning efficiency (Sterile Systems Inc., Logan, Utah), oxaloacetate (0.15 mg/ml), pyruvate (0.05 mg/ml), bovine insulin (0.2 U/ml), penicillin (400 units/ml), streptomycin (400 μg/ml), and Fungizone (2 μg/ml). Cells were perfused from the spleens by injecting 15 ml of HY medium into the spleens through a 26-gauge needle. Red blood cells were lysed when 5 ml of ice-cold 0.17M $NH_4Cl$ was added to the cell suspension and the cells were held on ice for 10 minutes. Cold HY medium was added, the cells pelleted at 300×g for 10 minutes and then resuspended in fresh HY medium for counting. Three spleens were perfused and approximately $2.3\times10^8$ cells were obtained.

D. Preparation of Myeloma Cells for Fusion

The myeloma cells, SP2/0-Ag14, were obtained from the Salk Institute for Biological Studies, San Diego, Calif., and are described by Shulman et al. in *Nature,* Vol. 276, pp. 269–270 (1978), as originating from a hybrid between a BALB/c spleen cell and the myeloma cell line X63-Ag8. The cells do not produce immunoglobulin and they die in a medium supplemented with HAT. Cells are maintained in Dulbecco's Modified Eagle Medium with fetal bovine serum (10%), 2-mercaptoethanol ($10^{-5}$M) and 8-azaguanine (15 μg/ml) under 7% $CO_2$ at 37° C. Prior to the fusion, cells were subcultured each day for 3 days, removed from the culture dishes by pipetting medium over the surface of the dish, pelleted by centrifugation at 300×g, and resuspended in HY medium for counting.

E. Preparation of Peritoneal Macrophages

Macrophages are often used as feeder cells during the production of hybridomas. We used a method to stimulate the production of macrophages that was suggested in *Selected Methods in Cellular Immunology,* B. Mishell and S. Shiigi, Eds., W. H. Freeman and Co., San Francisco, pp. 6–8 (1980). BALB/c mice were inoculated intraperitoneally with 2 ml of 3% thioglycollate medium that had been held in the dark for several months. Six days after the injection, on the same day as the cell fusion, the mice were euthanized with chloroform. Macrophages were collected immediately by injecting 5 ml of phosphate buffered saline, with 5 units/ml of heparin, into the peritoneal cavity, massaging the peritoneum, and withdrawing the fluid. Cells were pelleted at 600×g and resuspended in HY medium for counting.

F. Production of Hybrid Cells (Fusion Technique)

An amount of the spleen cell suspension which contained $1\times10^8$ cells was mixed with an amount of the myeloma cell suspension which contained $1\times10^7$ cells. After low speed centrifugation for 10 minutes at 300×g to pack the cells, they were washed once in serum-free HY medium and pelleted by centrifugation at 300×g for 10 minutes in a round-bottomed tube. The supernatant fluid was removed completely and the pellet loosened by tapping the tube. Next, 0.2 ml of 50% (w/v) polyethylene glycol (MW 1300–1600), prepared in serum-free medium and warmed to 37° C., was added to the cells. The mixture was agitated gently, placed in the centrifuge within 2 minutes, and centrifuged at 300×g for 5½ minutes. The mixture was diluted gently with 5 ml of serum-free HY medium and then further diluted with 5 ml of HY medium containing fetal bovine serum (20%). Cells were pelleted by centrifugation at 300×g for 10 minutes and the supernatant discarded. Cells were resuspended in 20 ml of HY medium containing hypoxanthine (13.6 μg/ml) and thymidine (7.6 μg/ml). This suspension was added to the fused-cell suspension, mixed gently, and distributed into seven 96-well flat-bottomed microplates at 50 μl of suspension per 6-mm well. Plates were covered and held at 37° C. with 5% $CO_2$ and 95% humidity. The next day one drop of HY medium that contained hypoxanthine, aminopterin (0.18 μg/ml), and thymidine (HAT) was added to each well. About 7 days later small colonies of hybrids began to appear and when they reached 1.0–1.5 mm in diameter a capillary pipette was used to transfer cells from the center of such individual isolated colonies into a new 6-mm well. During this time and during the subsequent transfer of hybridomas for expansion into 16-mm wells the cells were maintained in HY-HAT medium.

G. Analysis of Hybridomas

The indirect fluorescent antibody test (IFAT) as described by Jochim et al. in *Proceedings of the American Association of Veterinary Laboratory Diagnosticians*, pp. 91-103 (1974), was used to evaluate spent culture fluids recovered from hybridomas transferred to and growing in 16-mm wells. Undiluted fluids were tested on virus-infected, acetone-fixed monolayers of African green monkey kidney (Vero) cells grown in 8-chambered slides (Miles Laboratories, Inc., Naperville, Ill.). Fluorescein isothiocyanate (FITC)-labeled rabbit anti-mouse IgG, (Miles Laboratories, Inc., Elkhart, Ind.) was added to the primary antigen-antibody reaction in order to visualize the antigen with reflected light fluorescence microscopy. Fluids of interest were tested on cells infected with the homologous EHDV serotype 2 (strain Alberta), as well as heterologous BTV serotype 10 (strain BT-8) in order to evaluate the presence of cross-reactive antibodies to this antigenically-related *Orbivirus*. Controls for the test included uninfected Vero cells.

Of the 233 hybridomas that were identified microscopically and transferred from the original 6-mm wells, there were 156 that continued to grow in the new wells. However, only 136 of the heartiest hybridomas were selected to be tested by IFAT, and 24 of these were positive against the homologous virus in EHDV-infected Vero cell cultures. When culture fluids from these IFAT-positive hybridomas were tested against BTV-infected Vero cell cultures, ten did not react; seven reacted with antigenic determinants that apparently are shared by these two distinct orbiviruses. Three hybridomas, identified as 11C6, 12C9, and 12D5 and shown to secrete antibody to the homologous EHD viral antigen, were tested further by the IFAT with Vero cells infected with EHDV serotype 1 (strain New Jersey) and BTV serotypes 11, 13, and 17. Antibody secreted by these three hybridomas was group-specific in the IFAT, as there was little difference in the staining characteristics among the Vero cells infected with the two serotypes of EHDV. Also, none of the Vero cells infected with any of the BTV serotypes showed evidence of fluorescence when stained with these three hybridomas; similar negative results were seen with the uninfected Vero cell cultures. Cells from each of the IFAT-positive hybridomas were frozen in growth medium that contained fetal bovine serum (50%) and dimethylsulfoxide (10%). Subsequently, several hybridomas of interest were retrieved from liquid nitrogen storage and cloned to produce colonies of single antibody secreting cells.

H. Cloning of Hybridomas

In an effort to assure that the antibody secreted by a hybridoma is in fact monospecific, it is necessary to disperse the population of cells so that a cell line can be established from a single cell. The method used here was that of limiting dilution and it was used to clone the hybridomas 11C6 and 12D5. First the hybridomas were harvested, pelleted by low speed centrifugation, resuspended in HY-HAT medium and counted to determine the number of live cells. Then 5 ml cell suspensions were made that each contained 1, 10, 100, and 1,000 cells per ml and 50 µl amounts of such a suspension added to 200 µl of HY-HAT medium in each well of a 96-well flat-bottomed microplate. Cell cultures were held at 37° C. under 6% $CO_2$ and 95% humidity and observed each day for evidence of a single coloqy of cells that appeared to develop from a single cell. When a single colony in one well was about 1.0-1.5 mm in diameter the center of the colony was transferred to a 3-mm well in a new plate. The entire contents of the well was later transferred to a 6-mm well and then to a 16-mm well. Spent culture fluids were tested as previously described for the hybridoma cultures.

I. Analysis of Clones

There were 5 clones isolated from hybridoma 11C6 and they were maintained for several weeks in HY-HAT medium, which was recovered every 3-4 days and fresh medium added so that the antibody could be tested by the IFAT. Four of these 11C6 clones were positive with EHDV-infected Vero cells and did not react with BTV-infected cells. Culture fluid from one particular clone, 11C6.288, yielded an especially strong response with the IFAT. Antibody from this clone was tested against EHDV serotypes 1 and 2 and also with each of the five serotypes of BTV present in the United States, i.e., BTV types 2, 10, 11, 13, and 17. The monoclone was found to react to both serotypes of EHDV, but did not react to cells infected with any of the serotypes of BTV. Also, the monoclone did not react with uninfected Vero cells in the IFAT.

J. Production of Ascites in Histocompatible Mice

Clone 11C6.288 was shown to stimulate the production of ascites in histocompatible BALB/c mice. Adult female mice were stimulated by an intraperitoneal injection of 0.5 ml of pristane (2,6,10,14-Tetramethylpentadecane: Aldrich Chemical Co., Inc., Milwaukee, Wisc.). Two weeks later each mouse was inoculated with $1 \times 10^5$ or $1 \times 10^6$ cells in 0.5 ml of serum-free medium and 2 weeks later the first of several mls of ascitic fluid was recovered using an 18-gauge needle. Although the ascitic fluid was not titered to determine the monoclonal antibody concentration, we observed 4+ fluorescence, on a scale of 1 to 4, with the fluid diluted 1:50 and tested in the IFAT as previously described. By comparison, supernatant fluids are tested undiluted in the IFAT to achieve 4+fluorescence.

K. Characterization of Immunoglobulin

The isotype of the immunoglobulin secreted by clone 11C6.288 was determined by immunodiffusion in agarose. Culture fluid from the clone was added to 4-mm wells that were punched in the agarose in a pattern that consisted of a center well and 6 outside wells. The center well, also 4 mm in diameter and 2 mm from the outside wells (edge to edge) was filled with rabbit anti-mouse $IgG_1$, $IgG_{2a}$, or $IgG_{2b}$ (Miles Laboratories, Inc., Elkhart, Ind.). Precipitin lines that developed within 24 hrs were found to be against $IgG_{2a}$, thereby identifying clone 11C6.288 as producing this isotype of mouse immunoglobulin.

It is understood that the foregoing detailed description is given merely by way of illustration and that modification and variations may be made therein without departing from the spirit and scope of the invention.

Having thus described our invention, we claim:

1. A hybridoma which produces and secretes monoclonal antibody which is group-specific to epizootic hemorrhagic disease virus (EHDV) antigen and does not cross-react with bluetongue virus (BTV) antigen, said hybridoma further identified as ATCC HB 8378.

2. A method of producing a hybridoma which produces and secretes monoclonal antibody which is group-specific to EHDV antigen and does not cross react with BTV antigen, which comprises:
(a) immunizing mice with EHDV as follows: immunizing said mice with two intraperitoneal injections of $5.3 \times 10^6$ and $2.6 \times 10^6$ plaque forming units (PFU) of EHDV, given approximately 6 weeks apart; after 3 weeks, injecting said mice with $2.6 \times 10^6$ PFU of EHDV intravenously;
(b) removing spleens from said mice 3 days after the last injection of EHDV and making a suspension of the spleen cells;
(c) fusing sais spleen cells in the presence of a fusion promoter with mouse myeloma cells which lack hypoxanthine phosphoribosyl transferase to form hibridomas capable of producing monoclonal antibody;
(d) diluting and culturing said hybrodomas in separate wells in a medium which will support growth of only said hybridomas so that monoclonal antibody is secreted into said culture medium;
(e) testing said antibody-containing medium in each well containing a hybridoma for the presence of antibody which is group-specific to EHDV antigen and does not react with BTV antigen as follows:
(i)(a) reacting said antibody-containing medium with cell
cultures infected with EHDV serotypes 1 and 2;
(i)(b) reacting said antibody-containing medium with cell
cultures infected with BTV serotypes 2,10,11,13, and 17, and
(i)(c) reacting said antibody- containing medium with uninfected cell cultures;
(ii) reacting said reacted cultures of step (i) with fluorescein isothiocyanate conjugated antimouse IgG;
(iii) observing said reacted cultures of step (ii) using fluorescent light microscopy; and
(iv) selecting said antibody-containing medium in which said EHDV-infected cultures show fluorescence in step (iii); said BTV-infected cultures show no fluorescence in step
(iii), and said uninfected cell cultures show no fluorescence in step (iii); and
(f) cloning said hybridoma which is contained in said medium selected in step (e)(iv).

3. The hybridoma (prepared by) produced according to the method of claim 2.

4. The method of claim 2 which further includes:
(g) recovering said monoclonal antibody secreted by said hybridoma of step (f) by a method selected from the group consisting of (i) culturing said cloned hybridoma in a suitable medium and recovering the antibody from said medium, and (ii) culturing said cloned hybridoma intraperitoneally in mice and harvesting the malignant ascites or serum from said mice, which ascites or serum contains said antibody.

5. The monoclonal antibody produced according to the method of claim 4.

6. The monoclonal antibody of claim 5 in combination with immunochemicals.

7. The monoclonal antibody of claim 5 which is produced from a hybridoma formed by the fusion of SP2/0-Ag14 mouse myeloma cells and spleen cells from a mouse immunized with EHDV serotype 2 (strain Alberta).

8. The monoclonal antibody of claim 5 which is produced by the hybridoma identified as EHDV2XSP2/0-Ag14-11C6.288 and designated as ATCC HB 8378.

9. A method of diagnosing on animals without the occurence of false postive reactions to BTV using an indirect fluorescent antibody test (IFAT), which comprises:
(a) isolating virus from an infected animal to be diagnosed;
(b) growing said isolated virus in cell culture; and
(c) identifying EHD viral antigens in the isolated virus by applying the IFAT using monoclonal antibody which reacts to EHDV antigen of serotypes 1 and 2 as shown by the IFAT, does not react to BTV antigen of serotypes 2, 10, 11, 13, and 17 as shown by the IFAT, and does not react with uninfected Vero cultured cells used in the IFAT, in combination with fluorescein isothiocyanate conjugated rabbit anto-mouse IgH, and observing the EHDV antigen-antibody complex under ultraviolet light.

10. A method of diagnosing EHDV in animals without the occurence of false positive reactions to BTV using indirect fluorescent antibody test (IFAT), which comprises:
(a) isolating virus from an infected animal to be diagnoseds;
(b) growing said isolated virus in cell culture; and
(c) identifying EHD viral antigens in the isolated virus by applying the IFAT using monoclonal antibody produces and secreted by the hybridoma designated as ATCC HB 8387, in combination with fluorescein iosthiocynate conjugated rabbit anti-mouse IgG, and observing the EHDV antigen-antibody complex under ultraviolet light.

11. The method of claim 9 wherein said monoclonal antibody is produced and secreted by a hybridoma produced as follows:
(a) immunizing mice with EHDV as follows: immunizing said mice with two intraperitoneal injections of $5.3 \times 10^6$ and $2.6 \times 10^6$ plaque forming units (PFU) of EHDV, given approximately66 weeks apart; after 3 weeks, injecting said mice with $2.6 \times 10^6$ PFU of EHDV intravenously;
(b) removing the spleens from said mice 3 days after the last injection of EHDV and making a suspension of the spleen cells;
(c) fusing said spleen cells in the presence of a fusion promoter with mouse myeloma cells which lack hyposanthine phosphoribosyl transferase to form hybridomas capable of producing monoclonal antibody;
(d) diluting and culturing said hybridomas in separate wells in a medium which will support growth of only said hybridomas so that monoclonal antibody is secreted into said culture medium;
(e) testing said antibody-containing medium in each well containing a hybridoma for the presence of antibody which is group-specific to EHDV antigen and does not react woth BTV antigen as follows:
(i)(a) reacting said antibody-containing medium with cell cultures infected with EHDV serotypes 1 and 2;

(i)(b) reacting said antibody-containing medium with cell cultures infected with BTV serotypes 2, 10, 11, 13, and 17, and (i)(c) reacting said antibody-containing medium with uninfected cell cultures;

(ii) reacting said reacted cultures of step (i) with fluorescein isothiocyanate conjugated antimouse IgG;

(iii) observing said reacted cultures of step (ii) using fluorescent light microscopy; and (iv) selecting said antibody-containing medium in which said EHDV-infected cultures show fluorescence in step (iii); said BTV-infected cultures show no fluorescence in step (iii), and said uninfected cell cultures show no fluorescence in step (iii); and (f) cloning said hybridoma which is contained in said medium selected in step (e)(iv).

\* \* \* \* \*